US00PP17047P2

(12) United States Plant Patent
Kordes

(10) Patent No.: US PP17,047 P2
(45) Date of Patent: Aug. 22, 2006

(54) HYBRID TEA ROSE PLANT NAMED 'KORCOLUMA'

(50) Latin Name: *Rosa hybrida*
Varietal Denomination: KORcoluma

(75) Inventor: Tim-Hermann Kordes, Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 11/071,750

(22) Filed: Mar. 2, 2005

(51) Int. Cl.
*A01H 5/00* (2006.01)

(52) U.S. Cl. ..... Plt./139

(58) Field of Classification Search ..... Plt./139
See application file for complete search history.

(56) References Cited

PUBLICATIONS

Gemman PBR Application, ROS 2450, Apr. 5, 2004, W. Kordes' Söhne.

QZ (CPVO) Application, 20041556, Aug. 19, 2004, W. Kordes' Söhne.

*Primary Examiner*—Kent Bell
*Assistant Examiner*—June Hwu

(57) ABSTRACT

A new and distinct variety of rose with novel red flowers and attractive foliage with good disease resistance. It exhibits uniform upright to bushy growth. The new variety propagates well using traditional methods. This new and distinct variety has shown to be uniform and stable in the resulting generations from asexual propagation.

1 Drawing Sheet

CROSS REFERENCES AND FEDERAL R&D STATEMENT

There are no cross referenced or related applications. This variety was developed without the aid of any research grant.

Latin name of genus and species: The botanical classification of the new rose plant is *Rosa hybrida.*

Variety denomination: The denomination of the new variety is '*KORcoluma'*.

BACKGROUND OF THE INVENTION

The new variety of rose plant of the present invention originated from a controlled crossing in a breeding program of two distinct parents during the summer of 1994. The crossing was between 'Christoph Columbus', a non-patented rose and an un-named seedling.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORcoluma'.

SUMMARY OF THE INVENTION

The new rose plant may be distinguished from its seed parent, Christoph Columbus, by the following combination of characteristics:

1. The flowers of 'KORcoluma' are red while the flowers of the seed parent are salmon orange;
2. 'KORcolumna' has less vigorous growth; and
3. the flowers of 'KORcolumna' have more petals.

The new rose plant may be distinguished from its pollen parent, an un-named seedling by the following combination of characteristics:

1. The flowers of 'KORcoluma' are lighter red than the parent variety;
2. 'KORcoluma' has better disease resistance;
3. 'KORcoluma' has better branching and structure.

The objective of the hybridization was to create a new and distinct rose plant with unique qualities, such as:

1. Compact and uniform growth;
2. Abundant attractive, recurrent flowers;
3. Attractive and abundant foliage, and;
3. Resistance to diseases encountered in landscapes and gardens.

This combination of qualities is not present in prior rose cultivars. These objectives have been substantially achieved and in that distinguish 'KORcoluma' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORcoluma' was selected in May, 1995 from the seedling beds to be asexually propagated for further evaluation. The first asexual propagation of 'KORcoluma' was done by budding to seedling understocks in July, 1995 at the W. Kordes Söhne Nursery in Offenseth-Sparrieshoop, Germany.

This initial and other subsequent propagations conducted in controlled environments show that the foregoing and all other characteristics of 'KORcoluma' come true to form and are transmitted through succeeding generations.

BRIEF DESCRIPTION OF THE DRAWING

The accompanying color illustration shows as true as is reasonably possible to obtain in color photographs of this type, the typical characteristics of the buds, flowers, leaves, and stems of 'KORcoluma'. Specifically illustrated in SHEET ONE is a plant in bloom.

DETAILED BOTANICAL DESCRIPTION

The following is a description of 'KORcoluma', as observed in its growth in September, 2004 in a nursery in Jackson County, Oreg. on plants of one year of age. Color references are made using The Royal Horticultural Society (London, England) Colour Chart, 2001 except where common terms of color are used.

For a comparison, several physical characteristics of the rose variety 'KORmiach', a non-patented rose variety from the same inventor.

CHART 1

| | 'KORcoluma' | 'KORmiach' |
|---|---|---|
| Flower size | 80–100 mm | 100–120 mm. |
| Color | Red Group 46B. | Red Group 46B. |
| Fragrance | Light to moderate. | Light. |
| Height | 80–90 cm | 120–182 cm |

Parents:

*Seed parent.*—'Christoph Colombus'.

*Pollen parent.*—Un-named seedling.

Classification:

*Botanical classification.—Rosa hybrida, 'KORcoluma'.*

*Commercial classification.*—Hybrid Tea.

FLOWER AND FLOWER BUD

Blooming habit: Recurrent.

Flower bud:

*Size.*—Upon opening, 20–25 mm in length from base of receptacle to end of bud.

*Bud form.*—Pointed ovoid.

*Bud color.*—As sepals first unfold, bud color is Red Group 46A. When ¼ open, the upper surface of petals is Red Group 46A, and the lower surface is Red Group 46B.

*Sepals.*—Size: Average 25–45 mm long×8–10 mm wide. Shape: Moderate to moderately strong foliaceous appendages on three of the five sepals. Sepal apex is cirrose. Base is flat at union with receptacle. Quantity: Five. Surface texture: Upper and lower surfaces covered in fine hairs. Numerous stipitate glands present on margins. Color: Upper surface Green Group 137C. Upper surface of some sepals with intonations of Greyed-Purple Group 183C. Lower surface Green Group 137C.

Receptacle:

*Surface.*—Smooth.

*Color.*—Green Group 139C.

*Shape.*—Funnel.

*Size.*—6 mm (h)×8 mm (w).

Peduncle:

*Surface.*—Smooth or nearly so.

*Length.*—50–80 mm average length.

*Diameter.*—3–4 mm average diameter.

*Color.*—Green Group 139C. Intonations of Greyed-Purple Group 183C present.

*Strength.*—Strong.

*Borne.*—1–2 buds per flowering stem. Most commonly one.

Flower bloom:

*Fragrance.*—Light to moderate floral fragrance.

*Duration.*—On the plant 4–6 days. Senesced petals drop away somewhat.

*Size.*—Medium to large flowered garden rose. Average flower diameter is 80–100 mm when open.

*Form.*—Shape of flower when viewed from the side: Upon opening, upper part: Flattened convex to convex. Upon opening, lower part: Flattened convex. Open flower, upper part: Flattened convex. Open flower, lower part: Flat.

Color:

*Upon opening, petals.*—Outermost petals: Marginal zone Red Group 53A. Mid petal zone is 46B. Outer Side: Red Group 46B, with intonations of Red-Purple Group 58A in the mid petal zone. Inner Side: Red Group 46B. Innermost petals: Outer Side: Red Group 46B. Inner Side: Red Group 46B.

*Upon opening, basal petal spots.*—Basal petal spot, outermost petals: Outer Side: Yellow-Green Group 149C. Inner Side: Yellow-Green Group 149C. Basal petal spot, innermost petals: Outer Side: Yellow-Green Group 149C. Inner Side: Yellow-Green Group 149C.

*After opening, petals.*—Outermost petals: Marginal zone Red Group 53A. Mid petal zone is 46B. Outer Side: Red Group 46B, with intonations of Red-Purple Group 58A in the mid petal zone. Inner Side: Red Group 46B. Innermost petals: Outer Side: Red Group 46B. Inner Side: Red Group 46B.

*After opening, basal petal spots.*—Basal petal spot, outermost petals: Outer Side: Yellow-Green Group 149C. Inner Side: Yellow-Green Group 149C. Basal petal spot, innermost petals: Outer Side: Yellow-Green Group 149C. Inner Side: Yellow-Green Group 149C. Variegations: None.

General tonality: On open flower Red Group 46B. No change in the general tonality at the end of the $4^{th}$ day. Afterwards, general tonality is Red Group 46C.

Petals:

*Petal count.*—Approximately 25–30 petals under normal conditions.

*Petal reflex.*—Petals reflex slightly.

*Petal edge.*—Irregular.

*Petal shape.*—Apex: Round. Base: Round.

*Petal size.*—40–50 mm long; 35–45 mm wide.

*Thickness.*—Average.

*Petal arrangement.*—Generally in a regular pattern with overlapping edges.

*Petaloids.*—Present. Average of 2–3 per flower. Petaloids are 10 mm long and 3–4 mm wide. Color of inner side is Red Group 46B. Color of outer side is Red Group 46B. Surface texture is smooth. Shape is linear to elliptic.

Reproductive organs:

*Pistils.*—Average abundance. Approximately 70–90 present. Stigmas: Location: Superior in location to anthers. Color: Greyed-Yellow Group 160D. Styles: Length: 6–10 mm long. Color: Greyed-Yellow Group 179A.

*Stamens.*—Average 60–80 in number. Anthers: Size: Small. 1–2 mm long. Color: Greyed-Orange Group 164B. Pollen: Scant. Color: Greyed-Orange Group 164B. Filaments: Color: Orange-Red Group 32A. Length: 6–8 mm.

THE PLANT

Plant growth: Moderately vigorous. Compact and bushy. When grown as a budded nursery plant the average plant height is 80–90 cm and the average plant width is 50–70 cm.

Stems:

*Stem color.*—Young wood: Green Group 138B. Some stems with intonations of Greyed-Purple Group 184C. Older wood: Green Group 138B.

*Stem surface.*—Young wood: Smooth. Older wood: Smooth.

Prickles: Present.

*Incidence.*—Variable. 3–10 per 10 cm of stem.

*Size.*—Average length: 3–4 mm.

*Color.*—Immature and mature pickles Greyed-Green Group 195C. Immature prickles with intonations of Greyed-Red Group 179A. Prickles senesce to Greyed-Orange Group 177B.

*Shape.*—Concave with a slight downward angle.

Leaves and leaflets: Normally 5 leaflets on normal leaves in middle of the stem.

*Leaf size.*—100–120 mm (l)×85–100 mm (w).

*Quantity.*—Moderately abundant.

*Texture.*—Semi glossy. Average thickness.

*Color, mature foliage.*—Upper Leaf Surface: Green Group 139A. Lower Leaf Surface: Green Group 138B.

*Color, juvenile foliage.*—Upper Leaf Surface: Green Group 139A. Lower Leaf Surface: Green Group 138B.

*Anthocyanin intonation.*—Intonations of Greyed-Red Group 179A present on upper and lower surfaces of leaflets, leaf rachis, thorns, and petioles.

Stipules:

*Size.*—12 mm (l)–7 mm (w).

*Stipule color.*—Green Group 138B.

*Presence of stipitate glands.*—Present on margins.

*Margins.*—Bearded.

Petiole:

*Length.*—Variable. 5 mm–15 mm.

*Diameter.*—2 mm average diameter.

*Petiole color.*—Green Group 138A. Anthocyanin present on juvenile shoots. Greyed-Red Group 179A.

*Prickles.*—A few small prickles underneath.

*Stipitate glands.*—Limited numbers of stipitate glands on margins.

Petiole rachis:

*Color.*—Green Group 138A. Anthocyanin present on juvenile shoots. Greyed-Red Group 179A.

*Prickles.*—A few small prickles underneath.

*Stipitate glands.*—Limited numbers of stipitate glands on margins.

Leaflets:

*Size.*—Average size of the terminal leaflet is 50–60 mm(l)×35–40 mm(w).

*Shape.*—Round. Leaflet base: Rounded. Leaflet apex: Acute.

*Margins.*—Serrated.

*Texture.*—Average thickness.

Hips/seed formation: None observed.

Winter hardiness observation: To date, the new variety has been grown successfully in Zone 5.

Disease resistance: Above average resistance to powdery mildew, black spot, and rust diseases under normal growing conditions.

I claim:

1. A new and distinct variety of rose plant characterized by the following combination of characteristics:

(a) forms abundant, attractive red colored flowers;

(b) exhibits uniform upright to bushy growth habit;

(c) propagates well using traditional methods, and;

(d) exhibits above average disease resistance;

substantially as herein illustrated and described.

* * * * *

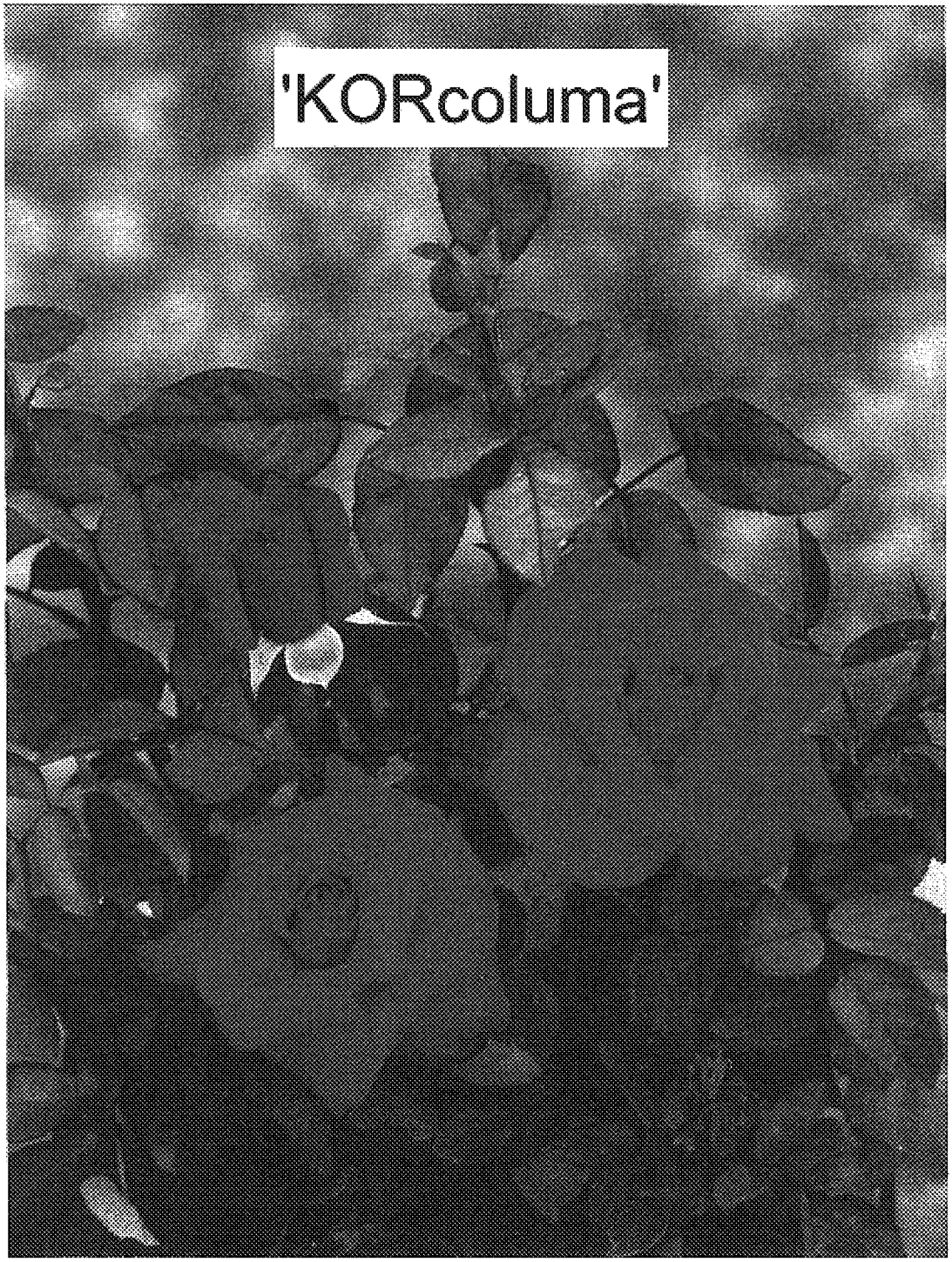
'KORcoluma'